(12) United States Patent
Quechuleno

(10) Patent No.: US 11,491,295 B2
(45) Date of Patent: Nov. 8, 2022

(54) NASAL CANNULA CLIP SYSTEM AND METHOD

(71) Applicant: Cynthia Quechuleno, Finlayson, MN (US)

(72) Inventor: Cynthia Quechuleno, Finlayson, MN (US)

(*) Notice: Subject to any disclaimer, the term of this patent is extended or adjusted under 35 U.S.C. 154(b) by 298 days.

(21) Appl. No.: 16/902,347

(22) Filed: Jun. 16, 2020

(65) Prior Publication Data
US 2021/0386952 A1  Dec. 16, 2021

(51) Int. Cl.
*A61M 16/06* (2006.01)

(52) U.S. Cl.
CPC .... *A61M 16/0683* (2013.01); *A61M 16/0666* (2013.01)

(58) Field of Classification Search
CPC .......... A61M 16/0868; A61M 16/0666; A61M 16/0683
See application file for complete search history.

(56) References Cited

U.S. PATENT DOCUMENTS

| | | | | |
|---|---|---|---|---|
| 5,704,916 | A  * | 1/1998  | Byrd ..................... | A61M 25/02 604/179 |
| 8,096,300 | B2 * | 1/2012  | Russo ............... | A61M 16/0497 128/207.14 |
| 8,336,551 | B1 * | 12/2012 | Preston ............. | A61M 16/0683 128/207.18 |
| 9,205,216 | B2 * | 12/2015 | O'Leary .......... | A61M 16/0666 |
| D791,308  | S  * | 7/2017  | Taylor ............... | A61M 16/1095 D24/128 |
| 9,788,989 | B2 * | 10/2017 | Weir ......................... | A61F 5/08 |
| 2003/0000533 | A1* | 1/2003 | Olsen ................ | A61M 16/1095 128/206.21 |
| 2007/0056590 | A1* | 3/2007 | Wolfson ............ | A61M 16/0666 128/207.18 |
| 2008/0190436 | A1* | 8/2008 | Jaffe ................. | A61M 16/0688 128/207.18 |
| 2008/0276941 | A1* | 11/2008 | Doty ................. | A61M 16/0666 128/207.18 |
| 2011/0197689 | A1* | 8/2011 | Haveri ................ | A61B 5/4818 73/866.5 |
| 2013/0146064 | A1* | 6/2013 | Dryden ............. | A61M 16/0666 128/207.18 |

* cited by examiner

*Primary Examiner* — Craig M Schneider
*Assistant Examiner* — David R Deal
(74) *Attorney, Agent, or Firm* — Uradnik Law Firm PC

(57) ABSTRACT

For a nasal cannula system, a pair of clip systems may be used to secure the legs of tubing loops placed about a patient's ears, wherein the size of each tubing loop may be adjusted by sliding a clip system along the length of the legs of the tubing loop.

15 Claims, 4 Drawing Sheets

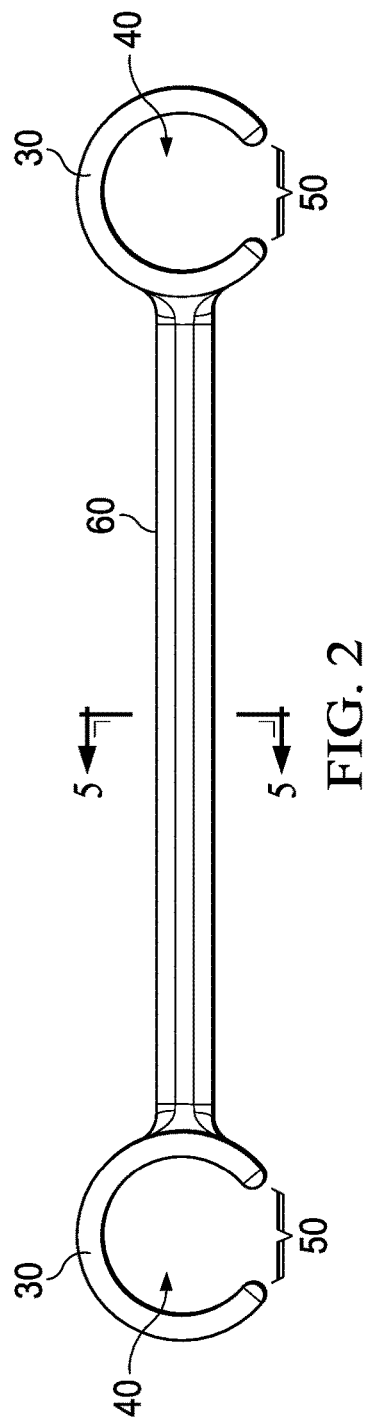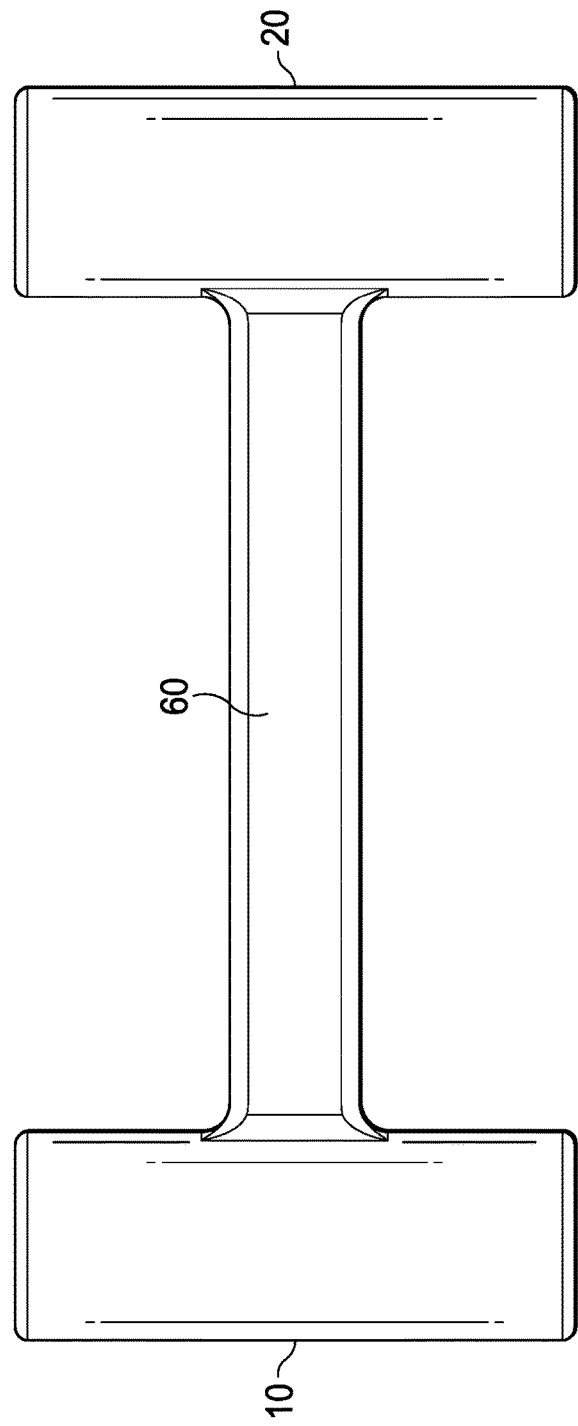
FIG. 2
FIG. 3

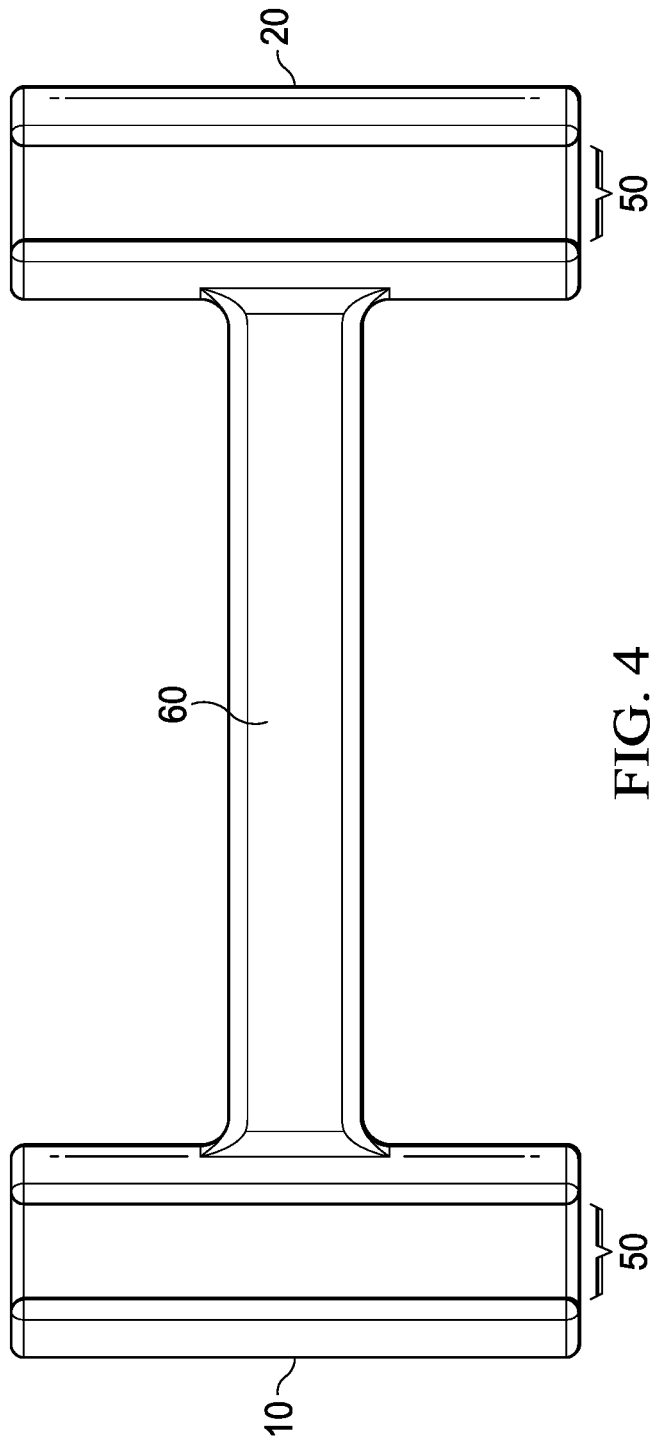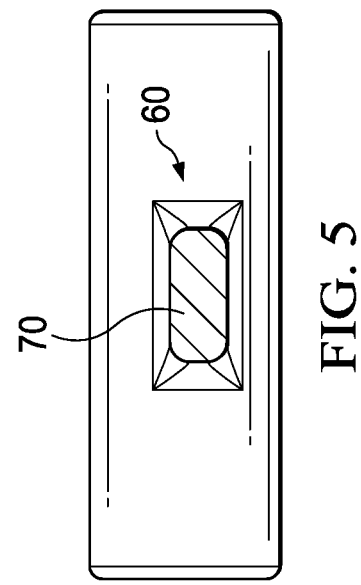
FIG. 4
FIG. 5

NASAL CANNULA CLIP SYSTEM AND METHOD

FIELD OF THE DISCLOSURE

The invention relates generally to a system and method for securing a nasal cannula in place on a patient.

BACKGROUND

A patient that requires oxygen (or other similar gases) often constantly fidgets with the tubing worn across her face or the nasal cannula inserted in her nose. More often than not, the cause of the discomfort originates from the cannula tubing that is routed behind the ears. The tubing is relatively hard in nature and generates pressure on the ear and cheek area, especially after prolonged periods of use.

Various attempts have been made to overcome these problems and alleviate these discomforts. Some care providers take foam padding and tape it to the earpieces to help alleviate the discomfort. Various other types of oxygen tube support devices have also been provided. Examples of such attempts can be seen by reference in several U.S. patents. U.S. Pat. No. 4,742,824, issued to Payton et al., describes an oxygen tube support patch having an adhesive face patch for support of the oxygen tube. U.S. Pat. No. 4,836,200, issued to Clark, discloses an oxygen tube support strap including a head strap having loops to hold the oxygen tubes. U.S. Pat. No. 5,704,916, issued to Byrd, discloses an oxygen tube support apparatus and associated method including a strap worn across the top of the head of a patient having two (2) opposite ends with adhesive sides for retaining the branches of the cannula between the adhesive ends. Another attempt can be seen in U.S. Pat. No. 8,336,551, issued to Preston et al., which discloses a cannula support device. Still other attempts include complex nasal oxygen delivery tubes, as seen in U.S. Pat. No. 4,915,104, issued to Marcy and U.S. Pat. No. 6,986,353, issued to Wright.

While these devices may achieve their particularly stated objectives, they each suffer from one (1) or more disadvantage or deficiency related to design or utilization. Particularly, the foam padding is known to turn and rollover thus causing additional discomfort and distraction to the patient. Strap devices worn over the head tend to shift when worn, especially when the patient is sleeping, which can dislodge the nostril prongs and add to discomfort and lack of oxygen being supplied to the patient. Complicated oxygen tubes can add additional time to set up and can be even more uncomfortable and obtrusive to the patient.

Thus, there remains a need for an improved system and method for holding a nasal cannula in place on a patient.

SUMMARY

The present disclosure provides a system and method for holding in place a nasal cannula. The system in one exemplary embodiment includes a pair of clips adapted to secure tubing looped around a patient's ear, with one clip positioned on each leg of the tubing loop. A cross member extends between the clips to keep the clips spaced apart, thus securing the tubing loop legs a desired distance apart.

Other benefits and advantages of the present disclosure will be appreciated from the following detailed description.

DESCRIPTION OF THE DRAWINGS

Exemplary embodiments of an exemplary system and method for securing in place a nasal cannula on a patient are shown in the accompanying drawings.

FIG. 2 is a side view of the exemplary nasal cannula clip system shown in FIG. 1.

FIG. 3 is a top view of the exemplary nasal cannula clip system shown in FIG. 1.

FIG. 4 is a bottom view of the exemplary nasal cannula clip system shown in FIG. 1.

FIG. 5 is a cross-sectional view of the exemplary nasal cannula clip system shown in FIG. 1, taken along the line 5-5 shown in FIG. 2.

DETAILED DESCRIPTION

Embodiments of the invention and various alternatives are described. Those skilled in the art will recognize, given the teachings herein, that numerous alternatives and equivalents exist which do not depart from the invention. It is therefore intended that the invention not be limited by the description set forth herein or below.

For convenience only, and without limitation, reference is made herein to nasal cannulas. However, the invention is not so limited. In addition to nasal cannulas, the system and method described herein may be used in other applications where it is desired to space apart two portions of tubing.

One or more specific embodiments of the system and method will be described below. These described embodiments are only exemplary of the present disclosure. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Further, for clarity and convenience only, and without limitation, the disclosure (including the drawings) sets forth exemplary representations of only certain aspects of events and/or circumstances related to this disclosure. Those skilled in the art will recognize, given the teachings herein, additional such aspects, events and/or circumstances related to this disclosure, e.g., additional elements of the devices described; events occurring related to securing tubing; etc. Such aspects related to this disclosure do not depart from the invention, and it is therefore intended that the invention not be limited by the certain aspects set forth of the events and circumstances related to this disclosure.

Figure 1:
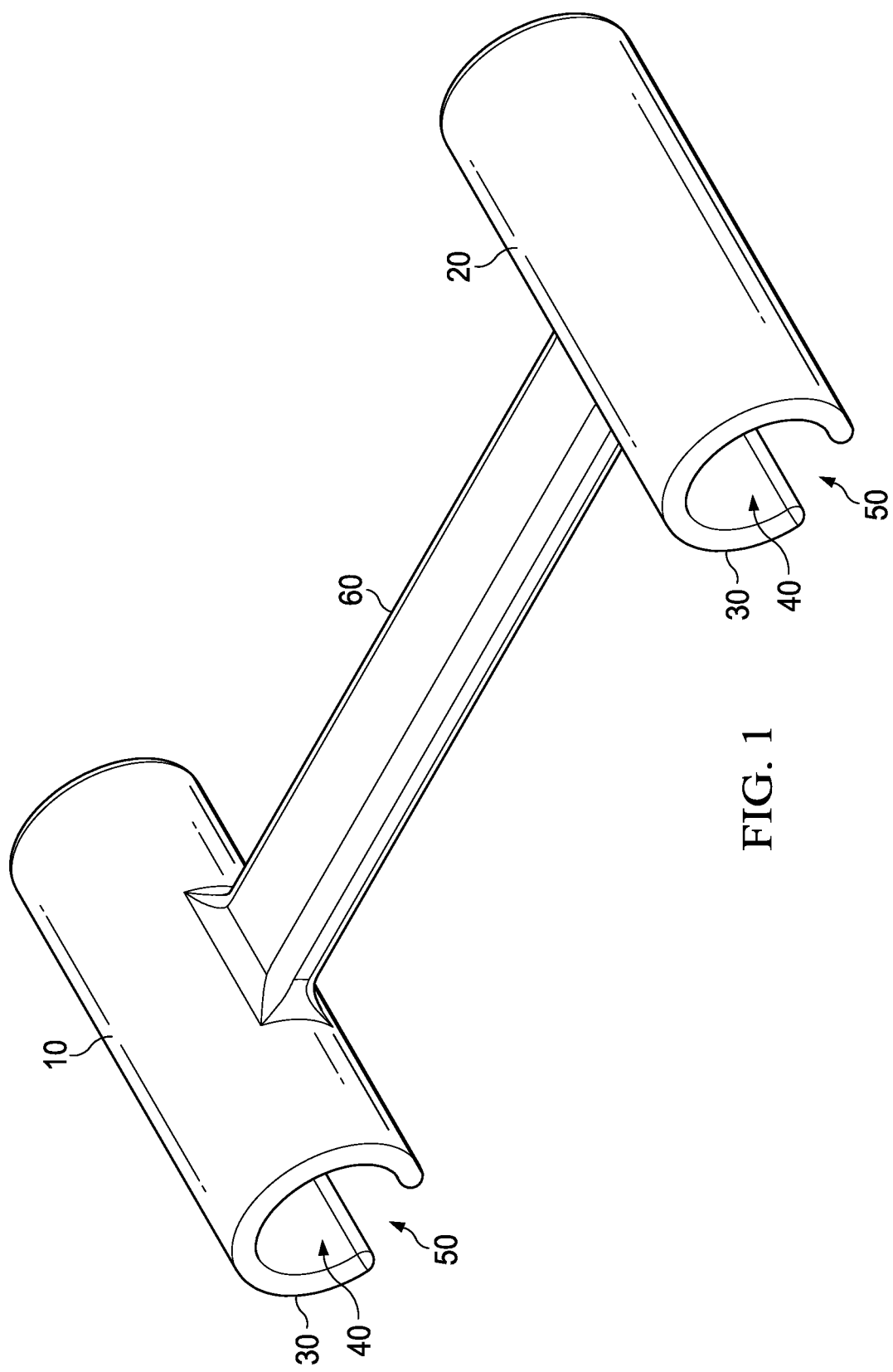
FIG. 1 is a perspective view of an exemplary nasal cannula clip system for use on the legs of a tubing loop placed about a patient's ear.

Turning now to the drawings, an exemplary system and method for securing in place a nasal cannula is provided. As shown in FIG. 1, the system includes first and second tubing clips 10, 20. The clips 10, 20 are generally cylindrically shaped and adapted for placement on a portion of tubing. Each clip 10, 20 includes a sidewall 30 forming a lumen 40 into which a tubing portion may be placed. The tubing portion is inserted through slot 50 in sidewall 30 and removably placed in the lumen 40. In one embodiment, the slot 50 is sized slightly smaller than the outer diameter of the tubing portion to be held. The tubing portion may be flexible for insertion through the slot 50. Alternately, or in addition, the sidewall may be flexible so that the slot 50 may be opened further from its resting state to accommodate passage of the tubing portion into lumen 40.

In one embodiment, a relatively rigid cross member 60 extends between the pair of clips 10, 20. The cross member 60 holds the clips 10, 20 apart. Thus, when tubing portions are inserted into clips 10, 20, the cross member 60 will space the tubing portions apart.

As shown in the drawings, the clips 10, 20 are generally parallel with each other, so that tubing portions inserted within the clips 10, 20 will be held in a parallel orientation. However, in alternated embodiments the clips 10, 20 may be offset or angled relative to one another to achieve a desired placement of tubing portions.

As shown in FIG. 5, in one embodiment the cross member 60 may include an insert 70 within all or a portion of itself. The insert may increase the weight of a clip 10, 20, to better hold in place the legs of a tubing loop placed about a patient's ear. The insert may also provide rigidity to the cross member 60 and help prevent the cross member 60 from bending along its length.

Figure 6:
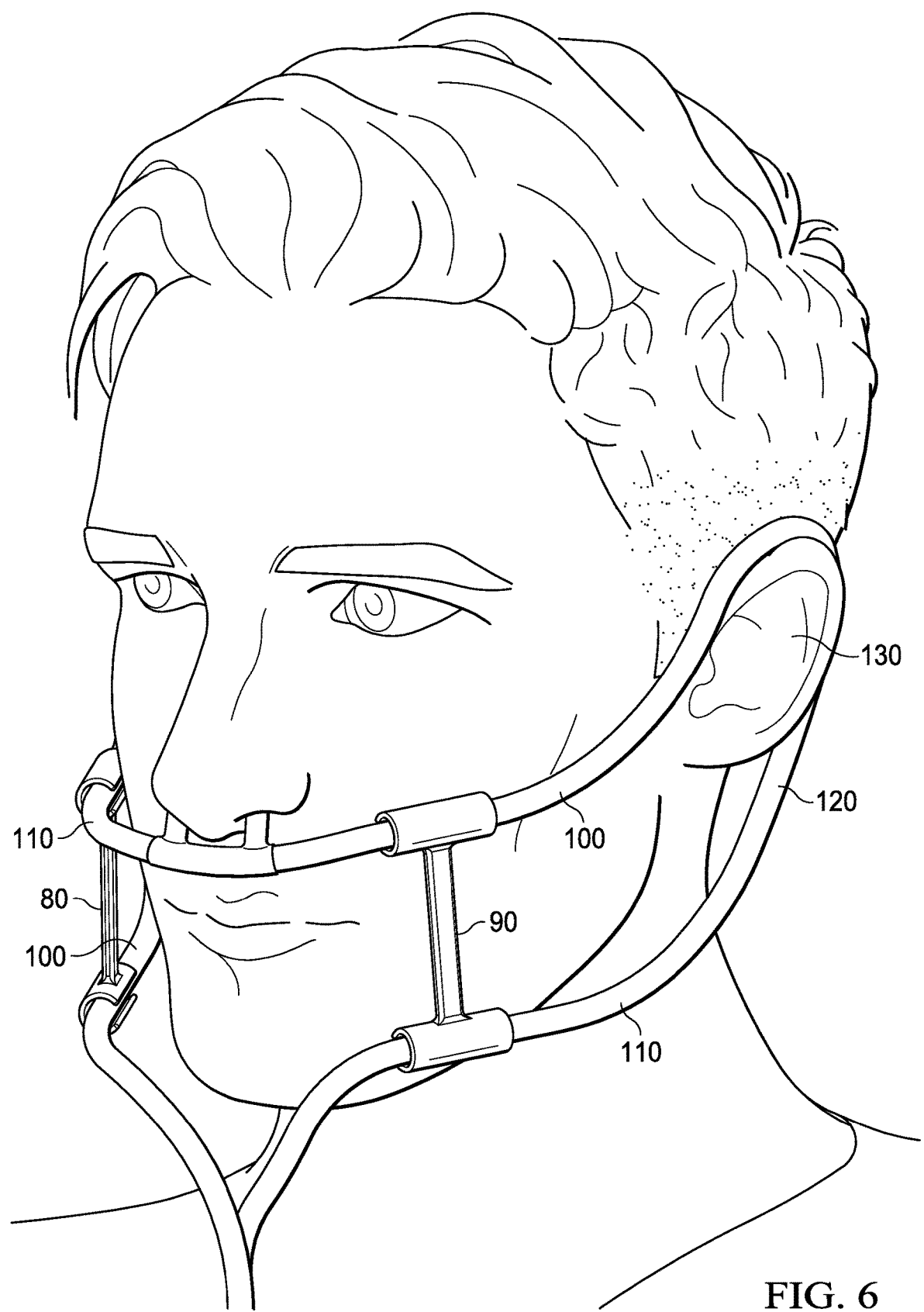
FIG. 6 is a perspective view of the use of two exemplary nasal cannula clip systems of the type shown in FIG. 1 to secure a nasal cannula in place on a patient.

As shown in FIG. 6, a pair of clip systems 80, 90 may be used to secure the legs 100, 110 of a tubing loop 120 placed about a patient's ear 130. In one embodiment, the size of loops 120 may be adjusted by sliding the clip systems 80, 90 along the length of the legs 100, 110 of tubing loop 120. In this way, a comfortable orientation of nasal cannula tubing may be achieved for a patient.

It should be understood that the foregoing description is only illustrative of the invention. Various alternatives and modifications can be devised by those skilled in the art having the benefit of this disclosure, without departing from the invention. Accordingly, the invention is intended to embrace all such alternatives, modifications and variances.

Certain exemplary embodiments of the disclosure may be described. Of course, the embodiments may be modified in form and content, and are not exhaustive, i.e., additional aspects of the disclosure, as well as additional embodiments, will be understood and may be set forth in view of the description herein. Further, while the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention.

What is claimed is:

1. A nasal cannula system including a clip system for securing the legs of a tubing loop for placement about a patient's ear, the clip system including a pair of clips spaced apart by a rigid cross member attached to each clip, each clip including a lumen formed by a generally cylindrical sidewall with a slot therein to permit a tubing portion to be removably inserted through the slot and into the lumen.

2. The nasal cannula system of claim 1, wherein the cross member includes an insert along all or a portion of the length of the cross member.

3. The nasal cannula system of claim 1, wherein the slot is sized slightly smaller than the outer diameter of the tubing portion to be removably inserted into the lumen.

4. The nasal cannula system of claim 1, wherein the slot includes a width that is smaller than a diameter of the lumen.

5. The nasal cannula system of claim 1, wherein the sidewall is flexible.

6. The nasal cannula system of claim 1, wherein the pair of clips are parallel to each other.

7. The nasal cannula system of claim 1, wherein the pair of clips are angled with respect to each other.

8. A nasal cannula system including a clip system for securing the legs of a tubing loop for placement about a patient's ear, the clip system including a pair of clips spaced apart by a cross member attached to each clip, each clip including a lumen formed by a generally cylindrical sidewall with a slot therein to permit a tubing portion to be removably inserted through the slot and into the lumen, wherein the cross member includes an insert along all or a portion of the length of the cross member.

9. The nasal cannula system of claim 8, wherein the cross member is rigid.

10. The nasal cannula system of claim 8, wherein the slot is sized slightly smaller than the outer diameter of the tubing portion to be removably inserted into the lumen.

11. The nasal cannula system of claim 8, wherein the slot includes a width that is smaller than a diameter of the lumen.

12. The nasal cannula system of claim 8, wherein the sidewall is flexible.

13. The nasal cannula system of claim 8, wherein the pair of clips are parallel to each other.

14. The nasal cannula system of claim 8, wherein the pair of clips are angled with respect to each other.

15. A nasal cannula system including a clip system for securing the legs of a tubing loop for placement about a patient's ear, the clip system including a pair of clips spaced apart by a rigid cross member attached to each clip, each clip including a lumen formed by a generally cylindrical flexible sidewall with a slot therein to permit a tubing portion to be removably inserted through the slot and into the lumen, wherein the cross member includes an insert along all or a portion of the length of the cross member, wherein the slot is sized slightly smaller than the outer diameter of the tubing portion to be removably inserted into the lumen, and wherein the pair of clips are parallel to each other.

* * * * *